United States Patent [19]

Devonald et al.

[11] Patent Number: 4,696,801

[45] Date of Patent: Sep. 29, 1987

[54] PROCESS FOR THE EXTRACTION OF METAL VALUES WITH BISIMIDAZOLE METAL EXTRACTANTS

[75] Inventors: David P. Devonald, Oldham; Anthony J. Nelson, Manchester; Peter M. Quan, Rochdale; David Stewart, Royton, all of England

[73] Assignee: Imperial Chemical Industries PLC, London, England

[21] Appl. No.: 828,748

[22] Filed: Feb. 12, 1986

[30] Foreign Application Priority Data

Feb. 25, 1985 [GB] United Kingdom ................. 8504819

[51] Int. Cl.⁴ ..................... C01G 51/00; C01G 3/00; C01G 9/00; C01G 11/00
[52] U.S. Cl. ................................ 423/24; 75/101 BE; 423/100; 423/139; 423/DIG. 14; 548/336
[58] Field of Search .................. 423/24, 99, 100, 139, 423/DIG. 14; 75/101 BE

[56] References Cited

U.S. PATENT DOCUMENTS

| | | | |
|---|---|---|---|
| 3,843,667 | 10/1974 | Cupery | 423/24 X |
| 4,039,612 | 8/1977 | Price et al. | 423/24 |
| 4,202,944 | 5/1980 | Hancock et al. | 423/24 X |
| 4,576,815 | 3/1986 | Robinson | 423/658.5 |
| 4,581,220 | 4/1986 | Nelson et al. | 423/658.5 |

OTHER PUBLICATIONS

*Chemical Abstracts,* 77:48462u (1972), [Ger. Offgn. No. 2,149,825, 4/13/72, Melloni et al.].

*Primary Examiner*—Richard A. Schwartz
*Attorney, Agent, or Firm*—Cushman, Darby & Cushman

[57] ABSTRACT

Metal values are extracted from aqueous solutions containing halide or pseudohalide anion using 1,1'-substituted 2,2'-biimidazole or bibenzimidazole compounds. Useful for the solvent extraction of zinc and copper from chloride leach solutions.

18 Claims, No Drawings

PROCESS FOR THE EXTRACTION OF METAL VALUES WITH BISIMIDAZOLE METAL EXTRACTANTS

This invention relates to a process for the extraction of metal values from aqueous solutions of metal salts, and in particular to a process for the extraction of metal values from aqueous solutions in the presence of halide anions.

The use of solvent extraction techniques for the hydrometallurgical recovery of metal values from metal ores has been practised commercially for a number of years. For example copper may be recovered from oxide ores or from ore tailings by treating the crushed ore with sulphuric acid to give an aqueous solution of copper sulphate which is subsequently contacted with a solution in a water-immiscible organic solvent of a metal extractant whereby the copper values are selectively extracted into the organic phase.

The application of solvent extraction techniques to aqueous solutions containing halide anions however has presented numerous technical problems. For example copper bearing sulphur-containing ores such as chalcopyrite may be leached using ferric chloride or cupric chloride solutions, but the solvent extraction of the resultant leach solutions presents formidable difficulties. The recovery of zinc by solvent extraction from halide-containing solutions such as those derived from sulphur-containing ores by chloride leaching has also been proposed (See for example, G. M. Ritcey, B. H. Lucas and K. T. Price, Hydrometallurgy, 1982, 8, page 197). However, known extractants for zinc (for example organophosphorous compounds such as tributyl phosphate) generally show a poor efficiency of metal recovery and a poor selectivity for zinc over the iron present in such leach solutions.

The present invention provides a process for the extraction of metal values from aqueous solutions containing halide or pseudohalide ions by the use of metal extractants whose several properties meet the stringent requirements imposed on the extractant by the system.

According to the present invention there is provided a process for extracting metal values from aqueous solutions of metal salts containing halide or pseudo anions which comprises contacting the aqueous solution with a solution in a water-immiscible organic solvent of a biimidazole or bibenzimidazole of formula:

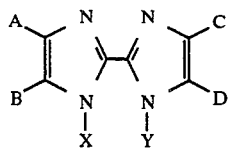
I wherein X and Y, which may the the same or different, taken together contain a total of from 12 to 52 saturated carbon atoms and are each selected from the group R—, RCO—, —CH$_2$CO.OR, —CH(CO.OR)$_2$ and —CO.OR wherein R is a hydrocarbyl group; or wherein X and Y taken together contain a total of from 12 to 52 saturated carbon atoms and taken together are selected from the groups

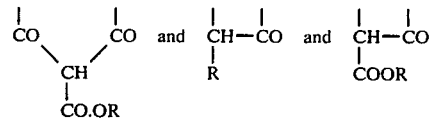

wherein R is a hydrocarbyl group; and wherein A, B, C and D, which may be the same or different are each hydrogen or a substituent Z wherein Z is lower alkyl, halogen, nitro, cyano or—CO.OR' wherein R' is lower alkyl; or A and B taken together with the two carbon atoms joining them form an optionally substituted cyclohexene ring and/or C and D taken together with the two carbon atoms joining them form an optionally substituted cyclohexene ring; or A and B taken together with the two carbon atoms joining them form an optionally substituted benzene ring and/or C and D taken together with the two carbon atoms joining them form an optionally substituted benzene ring.

The term 'lower alkyl' as used herein means an alkyl group containing from 1 to 6 carbon atoms and preferably from 1 to 4 carbon atoms.

The group R is preferably an alkyl, optionally substituted aryl, optionally substituted alkylaryl, optionally substituted arylalkyl, optionally substituted cycloalkyl or optionally substituted alkoxyalkyl. It is to be noted that X and Y may be the same or different, and hence different groups R may be present in X and Y. Especially preferred groups R are branched alkyl groups containing from 8 to 24 carbon atoms, provided that the groups X and Y together contain from 12 to 52 saturated carbon atoms.

The groups X and Y are preferably the same. Preferred groups X and Y are the group—CO.OR. Thus it is especially preferred that the groups X and Y are the same and are both—CO.OR wherein R is a branched chain alkyl group containing from 8 to 24 carbon atoms. Improved solubility in desired solvents may often be achieved when the group R is a mixture of alkyl groups and especially an isomeric mixture of alkyl groups containing the same number of carbon atoms.

When A and B taken together with the two carbon atoms joining them are optionally substituted cyclohexene rings, C and D may each be hydrogen or one of the substituents Z defined above. Alternatively, both A and B taken together with the two carbon atoms joining them and C and D taken together with the two carbon atoms joining them may be optionally substituted cyclohexene rings. As examples of optional substituents which may be present in the cyclohexene ring(s) there may be mentioned those substituents Z as defined above.

When A and B taken together with the two carbon atoms joining them are optionally substituted benzene rings, C and D may each be hydrogen or one the substituents Z defined above. Alternatively, both A and B taken together with the two carbon atoms joining them and C and D takan together with the two carbon atoms joining them may be optionally substituted benzene rings. As examples of optional substituents which may be present in the benzene ring(s) there may be mentioned those substituents Z as defined above. An especially preferred class of compounds of formula I above are 2,2'-bibenzimidazoles of formula:

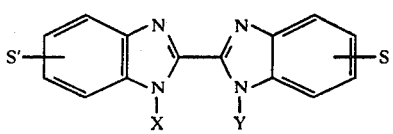

(II)

wherein S and S' are separately hydrogen or any of the substituents as defined above for Z. S and S' are preferably hydrogen, lower alkyl (for example methyl) or halogen. It is preferred that the 4 and 4' positions in the bibenzimidazole are free of substitution. Thus in especially preferred compounds of formula (II), S and S' are separately hydrogen or methyl (in a position other than 4,4', or 7,7') and X and Y represent the group CO.OR in which R is a hydrocarbyl group as defined. In a preferred group of such compounds, S and S' are hydrogen and X and Y are the same and are each the group—CO.OR wherein R is a branched primary alkyl group or an isomeric mixture of branched primary alkyl groups. By the term 'branched primary alkyl group' as that term is used herein is meant a branched alkyl group bearing two hydrogen atoms on the carbon atom linked to the oxygen atom in the group—CO.OR. We have found that such compounds generally have an especially high affinity for zinc combined with good selectivity against acid transfer.

2,2'-Biimidazole compounds for use in the present invention may be prepared by reaction of (optionally substituted) 2,2'-biimidazole with appropriate alkyl or acyl halides or alkylchloroformate to introduce the groups X and Y.

2,2'-Bibenzimidazole compounds for use in the present invention may be prepared by reaction of an appropriately substituted o-phenylenediamine with an appropriate derivative of oxalic acid. Trichloroacetonitrile or methyl trichloroacetamidate are particularly convenient as the oxalic acid derivative (Holan, Ennis and Hinde, J. Chem. Soc. (London), (C) 1967 page 20).

2-(2-Imidazolyl)-benzimidazole compounds for use in the present invention (that is compounds in which either A and B or C and D but not both form part of a benzene ring) may be prepared as described by Yutilov and Kovaleva (Russian Pat. No. 541846 -Chemical Abstracts No. 171448g Vol. 86, 1977) or by the procedure of Ennis, Holan and Samuel (J. Chem. Soc. (C), 1967 pages 33 to 39).

Compounds for use in the invention in which A and B taken together with the carbon atoms joining them and/or B and C taken together with the carbon atoms joining them represent cyclohexene rings may be prepared by catalytic hydrogenation of the corresponding benzenoid compounds or from the corresponding biimidazolines (Duranti and Balsamine, Synthesis 1974 page 815) or as described by Bernarducci et al, Inorganic Chemistry Volume 22, 1983, pages 3911 to 3920).

Highly branched primary alkyl groups R may be usefully derived from commercially available mixtures of branched aliphatic alcohols manufactured by the 'Oxo' process or from branched alcohols prepared by the Guerbet and Aldol condensations. Such Guerbet alcohols are primary alcohols characterised by branching at the position beta to the hydroxyl group and have the general formula:

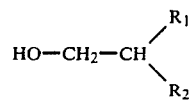

wherein $R_1$ and $R_2$ are both alkyl groups and $R_1$ contains two fewer carbon atoms than $R_2$. $R_1$ and $R_2$ may be straight chain or branched chain alkyl groups and may be isomeric mixtures of alkyl groups. A mixture of highly branched alcohols may be obtained by Guerbet or Aldol condensations of mixtures of alcohols and aldehydes respectively. By way of Example, good solubility in preferred organic solvents is conferred on biimidazole or bibenzimidazole compounds of formula (I) above wherein the group —R as defined in X and Y is derived from commercial isooctadecanol prepared by the aldol dimerisation of commercial nonanol and believed to consist essentially of a mixture of geometrical isomers of the compound (IV):

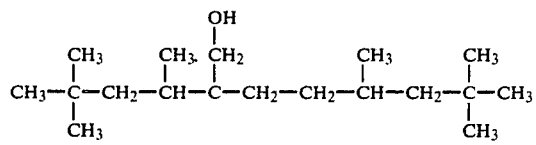

Such alcohols may be used directly to form the corresponding group—CO.OR. Alternatively the alcohols may be oxidised to carboxylic acids and thence converted to the corresponding acid chloride to introduce the group—CO.R, for example by reaction with 2,2'-bimididazoles as described above. It will be appreciated of course that once the alcohol is oxidised to the corresponding carboxylic acid, the derived alkyl group R will no longer be a primary alkyl group as defined above.

The process of the present invention may be applied to the extraction from aqueous solutions containing halide or pseudohalide ion of any metal capable of forming a stable halide or pseudohalide containing complex with the biimidazole or bibenzimidazole compound in the water-immiscible organic solvent. Examples of such metals include zinc, copper, cobalt, and cadmium. The process of the present invention is especially suitable for the solvent extraction of zinc and copper from aqueous solution obtained by the halide or pseudohalide leaching of sulphur containing ores. In general, such ores contain both copper and zinc in relative proportions which vary from ore to ore. It is convenient to recover both copper and zinc in successive processing stages from the leach solutions. For example the copper may be recovered from the leach solution by solvent extraction and the raffinate from this process may be treated in a separate solvent extraction process for the recovery of zinc. The process of the present invention may be used to recover either copper or zinc, although the same biimidazole or bibenzimidazole compound will not necessarily be used as the extractant in both cases. Preferably the process of the present invention is used in the zinc extraction stage only and a different solvent extractant (for example a solvent extractant disclosed in European Patent Application No. 0 057 797) used in the copper extraction stage.

It will be appreciated that the process of the present invention may be incorporated into a wide variety of different methods for the overall recovery of metals from their ores or from other metal-bearing sources. Details of these methods will vary depending on the metal concerned and the nature and composition of the leach solution. By way of example, an integrated process which is especially suitable for leach solutions containing high levels of cupric ion is described in European Patent Application No. 0 507 797.

The biimidazole or bibenzimidazole compounds for use in the present invention are especially useful for the recovery of zinc which has hitherto proved to be very difficult to recover effectively by solvent extraction. Thus the compounds of the present invention have in general a high affinity for zinc, which in general is combined with an excellent selectivity for zinc over acid and iron which are inevitably present in the leach solution especially for example when ferric chloride is used as leachant. However, even compounds which have a high affinity for zinc also retain a moderately high affinity for copper, and such reagents are not truly selective for zinc in the presence in high levels of copper. This is not a significant disadvantage in practice even when it is desired to recover zinc from a solution containing both copper and zinc, since the recovery of zinc generally takes place after the bulk of copper has been removed, for example in a first solvent extraction stage. If the reagent has a high affinity for both zinc and copper, it is perfectly feasible to remove residual copper remaining in the raffinate, for example by cementation using a metal such as zinc or iron, and to treat the resulting copper-free aqueous solution by solvent extraction to recover the zinc. However, the compounds of use in the process of the present invention generally show a surprisingly high relative selectivity for zinc over copper such that it may be possible to treat the solution remaining after copper solvent extraction without the need for an additional cementation step to remove residual copper.

The zinc solvent extraction circuit may be similar in design to that proposed in European Patent Application No. 0 057 797 for the recovery of copper from halide containing solutions by solvent extraction. Thus for example in a circuit for the recovery of copper and zinc from the aqueous leach solution derived from the leaching of a sulphur-containing ore with for example ferric chloride, the aqueous low-copper raffinate from the copper solvent extraction stage will contain zinc, iron and halide ion (for example 35 gpl zinc, 70gpl iron, 3.7 M in chloride ion and containing 5gpl hydrochloric acid). This feed to the zinc circuit may be contacted with a solution of the extractant of the present invention in a water immiscible organic solvent into which the zinc is extracted. The loaded organic phase solution is contacted with an aqueous strip solution containing a reduced level of zinc and halide ion such that at least a proportion of the zinc transfers into the aqueous strip phase. The stripped organic phase is returned to extract more zinc, and the loaded aqueous strip solution is passed to a zinc recovery stage, typically an electrowinning stage. The electrowinning stage may produce metallic zinc and chlorine gas (as described for example in 'Zinc Electrowinning from Chloride Electrolyte' by D. J. MacKinnon and J. M. Brannen; Mining Engineering April 1982 page 409) which may be used to regenerate the ferric chloride leachant (now reduced to ferrous ion). Alternatively an internal regeneration of the leachant may take place in a split cell without the generation of free chlorine gas. The zinc and chloride ion depleted aqueous stream from the electrowinning stage is returned to the strip stage to act as the aqueous strip solution, thereby completing the zinc extraction circuit.

The extraction process of the present invention may be represented by an equation such as the following:

$$L_{org} + M^{++}{}_{aq} + 2Cl^{-}{}_{aq} \rightleftharpoons (LMCl_2)_{org}$$

where M is a divalent metal ion such as zinc.

This equation is a grossly oversimplified representation of a very complex process and is not to be taken as in any way limiting the scope of the present invention, but it serves to illustrate the formation of a neutral organic phase complex of the divalent metal and the extractant (L) which is believed to predominate in the process of the present invention. The equation illustrates the reversible nature of the extraction, whereby the complex of the metal and the extractant in the organic phase can be stripped on contact with the aqueous solution from the electrowinning stage which is depleted in the metal and in the halide ion.

A further property which is of importance for an extractant in the process of the present invention is the absence of significant protonation by the acidic leach liquor. Such protonation may be represented by an equation such as:

$$L_{org} + H^{+}{}_{aq} + Cl^{-}{}_{aq} \rightleftharpoons (LH^{+}Cl^{-})_{org}$$

where L is the extractant. Such protonation of the ligand carries hydrochloric acid into the organic phase and builds up an excessive chloride ion concentration on the strip side. We have found that this problem is particularly acute for the extraction of zinc which is thought to promote the acid transfer. Preferred reagents of the present invention combine a high affinity for zinc with a low acid transfer into the organic phase.

As illustrated by the Examples, the extractants of the present invention provide a range of properties so that the optimum extractant may be selected for a given leach solution.

Examples of suitable water-immiscible organic solvents are aliphatic, aromatic and alicyclic hydrocarbons, chlorinated hydrocarbons such as perchloroethylene, trichloroethane and trichloroethylene. Mixtures of solvents may be used. Especially preferred in conventional hydrometallurgical practice are mixed hydrocarbon solvents such as high boiling, high flash point petroleum fractions (for example kerosene) with varying aromatic content. In general, hydrocarbon solvents having a high aromatic content, for example AROMASOL H which consists essentially of a mixture of trimethylbenzenes and commercially available from Imperial Chemical Industries PLC (AROMASOL is a trade mark) or SOLVESSO 150 commercially available from Esso (SOLVESSO is a trade mark), provide a higher solubility for the extractant and its metal complex, whilst kerosene having a relatively low aromatic content, for example ESCAID 100 which is a petroleum distillate comprising 20% aromatics, 56.6% paraffins and 23.4% naphthenes commercially available from ESSO (ESCAID is a trade mark) may in certain cases improve the hydrometallurgical performance of the extractant. Factors influencing the solubility of the extractant and its metal complex are complicated, but in general extractants having highly branched substituents and/or an isomeric mixture of substituents have comparatively high solubility. The concentration of the extractant in the water-immiscible organic solvent may be chosen to suit the particular leach solution to be treated. Typical values of extractant concentration in the organic phase are between about 0.1 to 2 Molar, and an especially convenient range is from 0.2 to 1.0 Molar in the organic solvent.

Certain biimidazole or bibenzimidazole for use in the present invention are novel compounds and the present invention includes such novel compounds.

The invention is illustrated by the following Examples in which all parts and percentages are by weight unless otherwise stated.

EXAMPLE 1

This Example illustrates the preparation and use of 1,1′-bis(tridecyloxycarbonyl)-2,2′-bimidiazole.

The tridecanol used in this Example was the commercially available mixture of isomeric branched-chain $C_{13}$ primary aliphatic alcohols manufactured by the oxo process. Tridecyl chloroformate was prepared by adding tridecanol (200g) dropwise during 75 minutes to liquid phosgene (160g) which was refluxing below a condenser cooled with a mixture of solid carbon dioxide and acetone. After addition was complete the mixture was stirred for 30 minutes. Excess phosgene was then allowed to evaporate into a scrubbing device charged with 20% aqueous sodium hydroxide. The last traces of phosgene were removed by bubbling nitrogen through the liquid while it was heated to 80°.

Tridecyl chloroformate (26.2g) was added dropwise to a stirred suspension of 2,2′-biimidazole (6.7g) in a mixture of dry methylene chloride (35cm$^3$) and dry pyridine (25cm$^3$) at such a rate that the temperature did not exceed 35°. After stirring for 16 hours at room temperature the reaction mixture was filtered and methylene chloride was distilled from the filtrate under reduced pressure. The residue was extracted with petroleum ether (200cm$^3$, bp 60–80°) and the petroleum extract was extracted with two equal volumes of hydrochloric acid (2M) and then with water until acid free. The petroleum solution was dried with magnesium sulphate and the solvent was distilled under reduced pressure yielding an oil (25.3g). The nmr spectrum of this oil, and titration of an aliquot with perchloric acid in acetic acid and acetic anhydride, confirmed that it comprised 65% by weight of 1,1′-bis(tridecyloxycarbonyl)-2,2′-biimidazole and 35% of tridecanol. It was used as an extractant without further purification.

The ability of this compound to extract copper and zinc from solutions containing chloride ion was investigated by the following general method:

An aqueous solution was prepared which was 0.1M in cupric chloride (6.35gpl copper), and 0.1M in hydrochloric acid and which contained 250gpl of calcium chloride dihydrate. This solution was then agitated for 1.5 minutes with an equal volume of a solution which was a 0.2M solution of the extractant in SOLVESSO 150. The layers were allowed to separate and settle, and were separately analysed for copper content. The transfer of copper from the aqueous to the organic phase was calculated as the percentage of the ligand taken up as the copper complex (assuming the complex $LCuCl_2$). The transfer of hydrochloric acid from the aqueous solution into the organic solution was calculated as the percentage of ligand that was protonated, (assuming the stoichiometry $LH^+Cl^-$). The test was repeated using different molarities of hydrochloric acid and different concentrations of calcium chloride, and the results are presented in Table 1.

A similar test was used to determine the ability of the extractant to extract zinc from aqueous solution. An aqueous solution was prepared which was 0.6M in zinc chloride (39.24gpl zinc) and 0.1 M in hydrochloric acid and which contained 176.5gpl of calcium chloride dihydrate (the calcium chloride concentration was adjusted to take account of the higher zinc chloride concentration). This solution was then agitated for 1.5 minutes with an equal volume of a solution which was a 0.2M solution of the extractant in SOLVESSO 150. The layers were allowed to separate and settle, and were separately analysed for zinc content. The transfer of zinc from the aqueous to the organic phase was calculated as the percentage of the ligand taken up as the zinc complex (assuming the complex $LZnCl_2$). The transfer of hydrochloric acid from the aqueous solution into the organic solution was calculated as the percentage of ligand that was protonated. The test was repeated using different molarities of hydrochloric acid and different concentrations of calcium chloride, and the results are presented in Table 2.

The results show that the product of this Example is a very powerful extractant for both zinc and copper. The results also show an exceptionally low degree of acid transfer from acidic solution containing zinc chloride.

EXAMPLE 2

This Example illustrates the preparation and use of 1,1′-bis(isooctadecyloxycarbonyl)-2,2-bibenzimidazole.

Following the general procedure of Example 1, isooctadecyl chloroformate was prepared by reacting isooctadecanol with phosgene. Isooctadecyl chloroformate (99.8g) was then reacted with a suspension of 2,2-bibenzimidazole (35.1g) in a mixture of dry methylene chloride (100cm$^3$) and dry pyridine (50cm$^3$) yielding after work up 1,1′-bis(isooctadecyloxycarbonyl)-2,2-bibenzimidazole (124g, 86% purity) as a viscous oil.

The compound was evaluated as an extractant for copper and zinc using the procedure of Example 1 and the results are presented in Tables 1 and 2 respectively. The results show that the compound has good affinity for zinc, with a very low level of acid transfer, and relatively low affinity for copper.

EXAMPLE 3

Following the procedures of Examples 1 and 2, 2-hexyldecyl chloroformate was prepared from 2-hexyldecanol and reacted with 2,2-bibenzimidazole to give 1,1′-bis(2-heptyldecyloxycarbonyl)-2,2′-bibenzimidazole as an oil in 82% purity.

The compound was evaluated as an extractant for copper and zinc using the procedure of Example 1 and the results are presented in Tables 1 and 2 respectively. The results show that this compound is very similar in properties to the product of Example 2. Compared with the product of Example 2 it showed faster phase disengagement during the tests.

EXAMPLE 4

Following the procedure of Example 2, tridecylchloroformate was reacted with 2,2′-bibenzimidazole to give 1,1′-bis(tridecyloxycarbonyl)-2,2′- bibenzimidazole in 86% purity.

The compound was evaluated as an extractant for copper and zinc using the procedure of Example 1 and the results are presented in Tables 1 and 2 respectively. The results show that this compound is similar in properties to the product of Example 2, but that it has the advantage of being a slightly stronger ligand for zinc. Like the product of Example 3, it was less viscous and showed good phase disengagement properties.

EXAMPLE 5

This Example illustrates the preparation and use of 1,1'-bis(isodecyloxycarbonyl)-2,2'-bibenzimidazole The isodecanol used in this Example was the commercially available mixture of isomeric branched chain $C_{10}$ primary aliphatic alcohols manufactured by the oxo process. Following the procedures of Examples 1 and 2, isodecyl chloroformate was prepared from isodecanol and reacted with 2,2'-bibanzimidazole to give 1,1'-bis-(isodecyloxycarbonyl)- 2,2'-bibenzimidazole in 65% purity.

The compound was evaluated as an extractant for copper and zinc using the procedure of Example 1 and the results are presented in Tables 1 and 2 respectively. The results show that this compound is similar to the product of Example 4.

EXAMPLE 6

This Example illustrates the preparation and use of dimethyl substituted 1,1'-bis(tridecyloxylcarbonyl)-2,2'-bibenzimidazole.

A mixture of isomeric dimethyl-2,2'-bibenzimidazoles was prepared as follows. 40.7g of a mixture comprising commercially available 1,2-diamino-4-methylbenzene (66% w/w) and 1,2-diamino-3-methylbenzene (33% w/w) was dissolved in methanol. The solution was stirred and methyl 2,2,2-trichloroacetimidate (20.6cm³) was added dropwise during 30 minutes at 17°. Stirring was continued for 16 hours and the mixture was then boiled under reflux for 30 minutes, and then allowed to cool. The precipitate was collected, washed with methanol and dried yielding a pale fawn solid (18.2g, mp 286–291°).

This material was reacted with tridecyl chloroformate using the procedure of Example 2, yielding an oil in 81% purity having the general formula given below which represents an isomeric mixture of dimethyl substituted compounds:

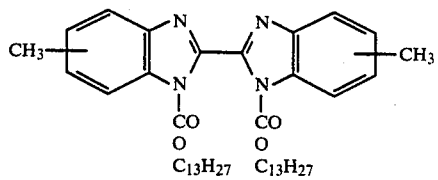

This mixture was evaluated as an extractant for copper and zinc using the procedure of Example 1 and the results are presented in Tables 1 and 2 respectively. The results show that whilst this mixture is a rather weaker liqand for zinc than the products of Examples 1 to 5, it shows excellent freedom from acid transfer

TABLE 1

| Example | HCl Molarity | CaCl$_2$.2H$_2$O (g/l) | % Uptake from 0.1 M CuCl$_2$ Copper | HCl |
| --- | --- | --- | --- | --- |
| 1 | 0.1 | 250 | 49 | 0 |
| 2 | 0.1 | 250 | 0 | 0 |
|   | 0.1 | 700 | 5 | 0 |

TABLE 1-continued

| Example | HCl Molarity | CaCl$_2$.2H$_2$O (g/l) | % Uptake from 0.1 M CuCl$_2$ Copper | HCl |
| --- | --- | --- | --- | --- |
|   | 1.0 | 700 | 4 | 2 |
| 3 | 0.1 | 250 | 0 | 0 |
|   | 1.0 | 700 | 6 | 3 |
| 4 | 0.1 | 250 | 0 | 0 |
|   | 1.0 | 700 | 7 | 1 |
| 5 | 0.1 | 250 | 0.5 | 0 |
|   | 1.0 | 700 | 6.5 | 1.5 |
| 6 | 0.1 | 250 | 0 | 0 |
|   | 1.0 | 700 | 5 | 1 |

TABLE 2

| Example | HCl Molarity | CaCl$_2$.2H$_2$O (g/l) | % Uptake from 0.6 M ZnCl$_2$ Zinc | HCl |
| --- | --- | --- | --- | --- |
| 1 | 0.01 | 176.5 | 97 | 0 |
|   | 0.01 | 626.5 | 98 | 0 |
|   | 0.10 | 626.5 | 97.5 | 0 |
| 2 | 0.01 | 176.5 | 23 | 0 |
|   | 0.01 | 626.5 | 33 | 0 |
|   | 0.10 | 626.5 | 35 | 0 |
| 3 | 0.01 | 176.5 | 27.5 | 0 |
|   | 0.01 | 626.5 | 33 | 0 |
|   | 0.10 | 626.5 | 37 | 0 |
| 4 | 0.01 | 176.5 | 24.5 | 0 |
|   | 0.01 | 626.5 | 33.5 | 0 |
|   | 0.10 | 626.5 | 37 | 0 |
| 5 | 0.01 | 176.5 | 23 | 0 |
|   | 0.01 | 626.5 | 31 | 0 |
|   | 0.10 | 626.5 | 32.5 | 0 |
| 6 | 0.01 | 626.5 | 19 | 0 |
|   | 0.10 | 626.5 | 20 | 0 |

EXAMPLE 7

This example demonstrates the selectivity of a typical compound of the invention in extracting zinc from an aqueous feed solution containing other metal impurities. The feed solution corresponded to the liquor obtained by (i) leaching a complex sulphide ore with ferric chloride solution and (ii) removing copper originally present in the liquor, for example by solvent extraction. The Example also demonstrates that the zinc can be stripped from the loaded organic solution by contact with a dilute aqueous solution of zinc chloride so as to give a more concentrated and purified aqueous solution of zinc chloride suitable as an advance electrolyte for the electrowinning of zinc. The dilute solution of zinc chloride used in stripping is representative of the spent electrolyte recovered after electrowinning has taken place.

A first feed solution was prepared to contain 5gpl HCl and the amounts of each metal listed in the first row of Table 3. A second more strongly acidic feed solution was made up having the same metal contents, but 20gpl HCl. The first feed solution was contacted by stirring for 15 minutes with an equal volume of a 0.5 molar solution of the product of Example 2 in ESCAID 100. The organic layer was separated and then stripped by contacting with an equal volume of an aqueous solution containing 15gpl zinc (as ZnCl$_2$) and 5gpl HCl. The aqueous solution was then separated and analysed for metals by atomic absorption spectroscopy with the results listed in the second row of Table 3. This procedure was repeated with the second, more acidic, feed solution, yielding an advance electrolyte having the composition listed in the third row of Table 3.

TABLE 3

| | $Zn^{II}$ | $Fe^{II}$ | $Pb^{II}$ | $Sb^{III}$ | $Sn^{II}$ | $Cd^{II}$ | $As^{III}$ | $Ag^{I}$ | $Co^{II}$ | $Ni^{II}$ |
|---|---|---|---|---|---|---|---|---|---|---|
| Feed Composition | 35 gpl | 75 gpl | 1.6 gpl | 140 ppm | 40 ppm | 110 ppm | 180 ppm | 30 ppm | 30 ppm | 70 ppm |
| Advance Electrolyte (from 5 gpl HCl feed) | 23.5 gpl | 7 ppm | 7 ppm | 5 ppm | 2 ppm | 0.6 ppm | <2 ppm | 2 ppm | <1 ppm | <0.5 ppm |
| Advance Electrolyte (from 20 gpl HCl feed) | 22.5 gpl | 8 ppm | 2 ppm | 13 ppm | 4 ppm | 0.7 ppm | 4 ppm | 1 ppm | <1 ppm | <0.5 ppm |

We claim:

1. A process for extracting metal values from aqueous solutions of metal salts containing halide or pseudo halide anions which comprises contacting the aqueous solution with a solution in a water-immiscible organic solvent of a biimidazole or bibenzimidazole extractant of formula:

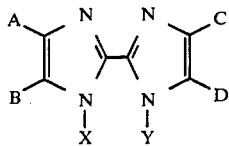

wherein X and Y, which may be the same or different, taken together contain a total of from 12 to 52 saturated carbon atoms and are each selected from the group R—, RCO—, —CH$_2$CO.OR, —CH(CO.OR)$_2$ and —CO.OR wherein R is a hydrocarbyl group; or wherein X and Y taken together contain a total of from 12 to 52 saturated carbon atoms and taken together are selected from the groups

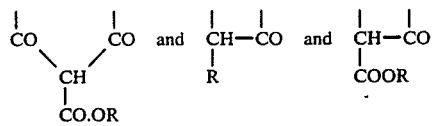

wherein R is a hydrocarbyl group; and wherein A, B, C which may be the same or different are each hydrogen or a substituent Z wherein Z is lower alkyl, halogen, nitro, cyano or—CO.OR' wherein R' is lower alkyl; or A and B taken together with the two carbon atoms joining them form an optionally substituted cyclohexene ring and/or C and D taken together with the two carbon atoms joining them form an optionally substituted cyclohexene ring; or A and B taken together with the two carbon atoms joining them form an optionally susbstituted benzene ring and/or C and D taken together with the two carbon atoms joining them form an optionally substituted benzene ring.

2. A process according to claim 1 wherein the group R is an alkyl, optionally substituted aryl, optionally substituted alkylaryl, optionally substituted arylalkyl, optionally substituted cycloalkyl or optionally substituted alkoxyalkyl.

3. A process according to claim 1 wherein the groups R are the same and are branched alkyl groups containing from 8 to 4 carbon atoms, provided that the groups X and Y together contain from 12 to 52 carbon atoms.

4. A process according to claim 1 wherein X and Y are the group COOR and R is a branched chain alkyl group containing from 8 to 24 carbon atoms.

5. A process according to claim 1 wherein the groups R are a mixture of isomeric alkyl groups.

6. A process according to claim 1 wherein A and B taken together with the two carbon atoms joining them are optionally substituted cyclohexene rings, C and D are each hydrogen or one of the substituents Z.

7. A process according to claim 1 wherein A and B taken together with the two carbon atoms joining them and C and D taken together with the two carbon atoms joining them are optionally substituted cyclohexene rings.

8. A process according to claim 1 wherein A and B taken together with the two carbon atoms joining them are optionally substituted benzene rings, C and D are each hydrogen or one of the substituents Z.

9. A process according to claim 1 wherein A and B taken together with the two carbon atoms joining them and C and D taken together with the two carbon atoms joining them are optionally substituted benzene rings.

10. A process according to claim 1 wherein the extractant is of the formula

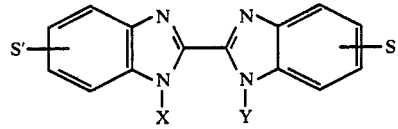

wherein S and S' are separately hydrogen or a substituent Z.

11. A process according to claim 10 wherein the X and Y represent the group COOR and S and S' are separately hydrogen or methyl.

12. A process according to claim 1 wherein the C0$_2$R group is derived from primary alcohols characterised by branching at the position beta to the hydroxyl group and have the general formula:

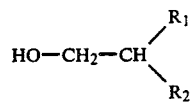

wherein R1 and R2 are both alkyl groups and R1 contains two fewer carbon atoms than R2.

13. A process according to claim 1 wherein the extractant is 1,1'-bis(tridecyloxycarbonyl)-2,2'-biimidazole.

14. A process according to claim 1 wherein the extractant is 1,1'-bis(isooctadecyloxycarbonyl)-2,2-bibenzimidazole.

15. A process according to to claim 1 wherein the extractant is 1,1'-bis(2-heptyldecyloxycarbonyl)-2,2'-bibenzimidazole.

16. A process according to claim 1 wherein the extractant is 1,1'-bis(tridecyloxycarbonyl)-2,2'-bibenzimidazole.

17. A process according to claim 1 wherein the extractant is 1,1'-bis(isodecyloxycarbonyl)-2,2'-bibenzimidazole.

18. A process according to claim 1 wherein the extractant is a dimethyl substituted 1,1'-bis(tridecyloxylcarbonyl)-2,2'bibenzimidazole.

* * * * *